United States Patent [19]
Carron et al.

[11] Patent Number: 5,327,211
[45] Date of Patent: Jul. 5, 1994

[54] PROCESS FOR MOLECULAR-SPECIFIC OPTICAL FIBER PROBES FOR RAMAN DETECTION

[76] Inventors: Keith T. Carron, 1121 Park Ave., Laramie, Wyo. 82070; Kenneth I. Mullen, 912 Garfield St., Laramie, Wyo. 82070

[21] Appl. No.: 788,900
[22] Filed: Nov. 7, 1991
[51] Int. Cl.$^5$ ............................ G01J 3/44; B05D 5/06
[52] U.S. Cl. .................................... 356/301; 427/163; 427/299; 427/419.1
[58] Field of Search .................... 427/163, 299, 419.1; 356/301

[56] References Cited

U.S. PATENT DOCUMENTS

| | | | |
|---|---|---|---|
| 4,395,312 | 7/1983 | McCreery et al. | 204/1 T |
| 4,573,761 | 3/1986 | McLachlan et al. | 350/96.24 |
| 4,674,876 | 6/1987 | Vo-Dinh | 365/124 |
| 4,758,298 | 7/1988 | Goorsky et al. | 427/163 |
| 4,781,458 | 11/1988 | Angel et al. | 356/301 |
| 4,804,930 | 2/1989 | Simic-Glavaski | 332/151 |
| 4,834,497 | 5/1989 | Angel | 350/96.29 |
| 4,913,934 | 4/1990 | Sharp et al. | 427/163 |
| 4,999,810 | 3/1991 | Vo-Dinh | 356/301 |
| 5,026,140 | 6/1991 | Russom | 427/163 |
| 5,063,178 | 11/1991 | Toomey | 427/163 |

OTHER PUBLICATIONS

Carron et al., "Selective-Ultratrace Detection of Metal Ions with SERS", 45, 420–423, Applied Spectroscopy (Apr. 1991).

Carron, K. T., "Surface Enhanced Resonance Raman, Resonance Hyper-Raman, and Hyper-Raman Spectroscopy of Molecules Adsorbed to Thin Metal Films; Chap 2: Experimental Techniques for Thin Film Surface Enhanced Resonance Raman Spectroscopy", Ph.D. Dissertation, Northwestern University, 1985 (no month).

*Primary Examiner*—Janyce Bell
*Attorney, Agent, or Firm*—John O. Mingle

[57] ABSTRACT

A process for indicator coating of SERS fiber-optic probes comprising selecting a potentially roughened probe which is enhanced with a deposited silver film and then treated by chemisorption on said probe to form a molecular-specific coating, such as by employing Eriochrome Black T for metal ions, octadecyl mercaptan for organics, or Cresol Red for pH.

26 Claims, 1 Drawing Sheet

PROCESS FOR MOLECULAR-SPECIFIC OPTICAL FIBER PROBES FOR RAMAN DETECTION

BACKGROUND OF INVENTION

1. Field of Invention

The present invention relates to a process for the making of molecular-specific optical fiber probe coatings for Raman spectroscopy, specifically SERS qualitative and quantitative detection of molecular or ionic species.

2. Background

Contaminant analysis of water is an important requirement and many current methods require the taking and removal of samples. This may inherently degrade the sample resulting in spurious results. For instance, in sampling groundwater exposure to air, contaminating collection procedures, or dirty sample containers may degrade the results. An in-situ, or direct, procedure is needed. Early attempts centered on fluorescence and absorption spectroscopy; however, SERS using fiber-optic probes has a great potential to satisfy this requirement.

Raman spectroscopy, particularly when surfaced enhanced which usually is referred to as SERS, is a proven and effective technique for qualitatively or quantitatively detecting specific chemical compounds within liquids. In Raman detection a probe light created by a laser excites molecules to higher energy states often in their vibrational energy bands. In returning to equilibrium, emission of Raman signal photons occur which characterize the molecular species. This emitted light can then be analyzed to determine the specie and its amount in the solution.

Surface enhancement of the Raman signals makes them orders of magnitude more intense and thus easier to detect; therefore, much lower concentrations can be resolved. Said enhancement is commonly achieved by adsorbed surface compounds containing silver, gold or copper. In many applications of SERS, optical fibers become the medium for transmitting light signals; thus, processing of said optical fibers may improve the SERS response.

Conventional Raman spectroscopy is well covered by D. A. Long's excellent treatise *Raman Spectroscopy*, McGraw-Hill 1977. A good review of SERS can be found in Keith T. Carron's dissertation, *Surface Enhanced Resonance Raman, Resonance Hyper-Raman, and Hyper-Raman Spectroscopy of Molecules Absorbed to Thin Metal Films*, Northwestern University 1985; Chapter 2, "Experimental Techniques for Thin Film SERRS", pages 13–45 is herein incorporated by reference, and hereinafter referred to as Carron (1985).

For the subject invention Raman spectroscopy is applied by calibration of the frequency shifts of the returning photon beam. These spectral peaks represent a specific molecular vibration which can be related to the peak height and correlates to the concentration of analyte. However, certain interferences occur between molecular species that mask the individual response peaks and make quantitative determinations especially uncertain. Further developments in Raman spectroscopy have tried to overcome this situation.

Recent U.S. patents covering the above mentioned concepts include;

| U.S. Pat. No. | Inventor | Year |
| --- | --- | --- |
| 4,395,312 | McCreery et al | 1983 |
| 4,573,761 | McLachlan et al | 1986 |
| 4,674,878 | V0-Dinh-1 | 1987 |
| 4,781,458 | Angel-1 et al | 1988 |
| 4,804,930 | Simic-Glavaski | 1989 |
| 4,834,497 | Angel-2 | 1989 |
| 4,999,810 | Vo-Dinh-2 | 1991 |

Referring to the above list, McCreery discloses electrochemically generated chromophores in solution that can be detected by Raman probes. McLachlan discloses a fiber-optic probe comprising separate transmitting and collecting optical fibers useful for Raman spectroscopy that have a specially designed angle of convergence. Vo-Dinh-1 discloses SERS substrate of cellulosic material coated with roughness-imparting latex-like microbodies and a metallized coating, preferably of silver, with a thickness of between about 100 to 2000 angstroms. Angel-1 discloses an optical fiber probe, or optrode, thinly coated with SERS metal at a thickness of about 10 to 50 angstroms, and additionally side-only coated over the metal with selectively absorbent material. Simic-Glavaski discloses a molecular electro-optical transistor and switch that can supplement Raman spectroscopy with electrical ionization designed to represent logical or switchable information. Angel-2 discloses a fiber-optic fluid detector designed for a specific material, such as a toxic fluid like gasoline. Vo-Dinh-2 discloses a data storage system using the principle of an SERS substrate as a means of accepting optical information.

The subject invention involves a method of producing optical fibers or fiber-optic probes coated with an appropriate chemical layer that selectively complexes or partitions desired molecules allowing SERS detection.

SUMMARY OF INVENTION

A purpose of the subject invention is to overcome the above deficiencies.

A further purpose is to allow in-situ qualitative and quantitative detection of desired compounds including those normally that do not posses vibrational modes. Metal ions, including hydrogen, are such a class of materials.

Another purpose is development of distinctive molecular-specific probe coatings that will enhance the SERS detection of required compounds or ions.

DETAILED DESCRIPTION OF INVENTION

The subject invention incorporates fiber-optic probe development. SERS can measure very small concentrations of certain compounds often with the aid of a molecular-specific coating. For instance, parts-per-billion, ppb, amounts are commonly measured, and in certain favorable circumstances even sub-ppb can be detected.

The molecular-specific coating for use with an SERS fiber-optic probe ideally must posses certain needed properties. Primarily it must bind to, complex with, adsorb to, or cause to be partitioned onto the probe surface, the desired molecule, specie, or analyte that is to be detected. Second, it must coat the fiber-optic probe sufficiently to cover the surface exposed to the in-situ measurements. Third, this coating must be stable, permanent and present a consistent response to the SERS measurements. Such coating can be potentially formed by one or more of the processes of absorption, chemisorption, and adsorption. Fourth, the coating must serve as a reference standard for quantitative measurements; i.e. difference in SERS bands associated with the coating and those associated with the coating-/analyte complex must be proportional to quantitative amounts of the analyte or detected specie.

Figure 1:
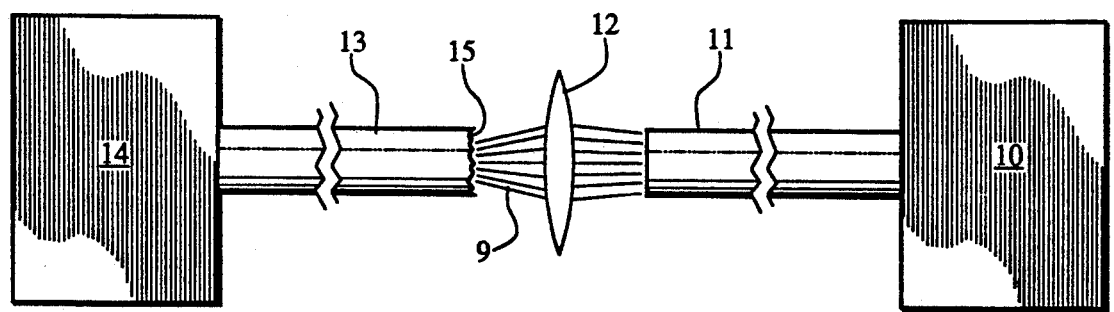
FIG. 1 shows a typical fiber-optic SERS probe system.
Figure 2:
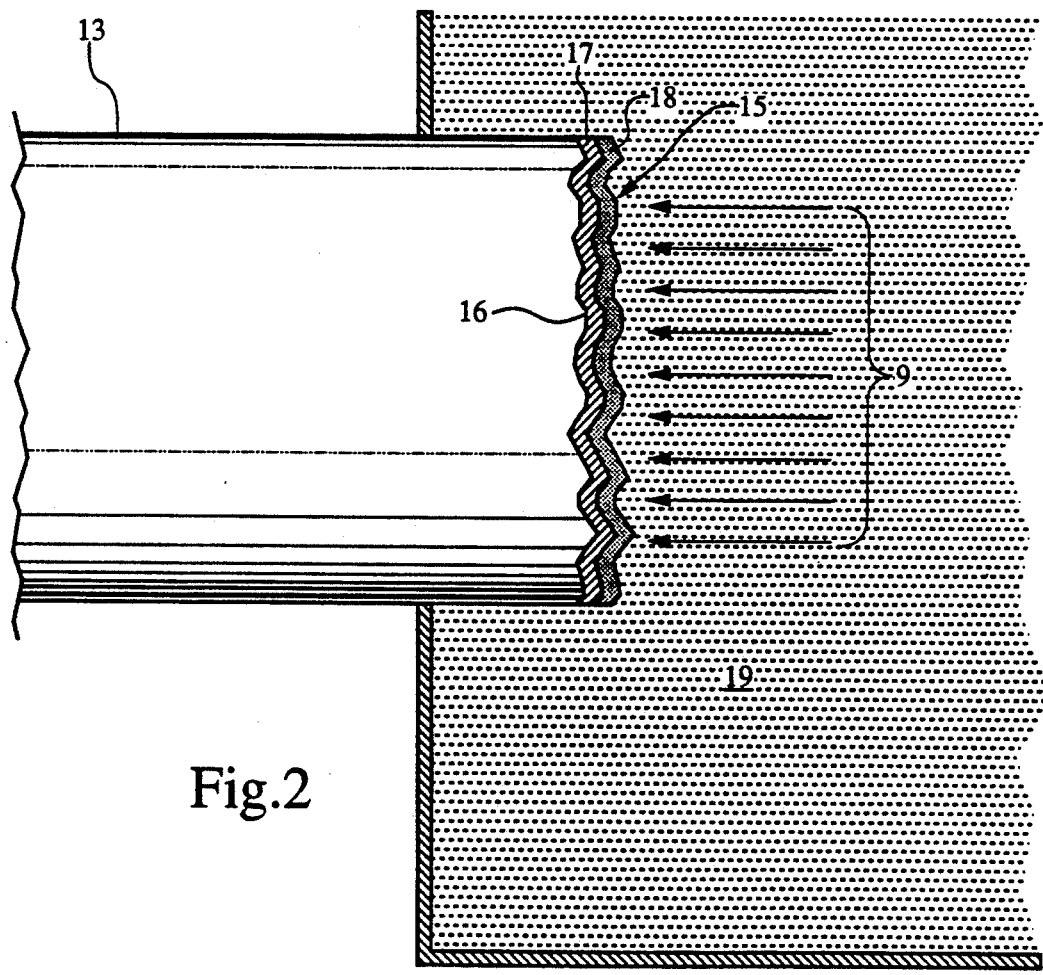
FIG. 2 shows the processed fiber-optic probe end.

The subject invention largely incorporates the chemical preparation of such molecular-specific coatings that employs Raman indicators or partitioning compounds. FIG. 1 shows a typical overall Raman spectroscopy system. The laser light source 10 is transmitted by the fiber-optic 11 to a lenses 12 which focuses the laser light 9 onto the detection fiber-optic 13, and in particular on the treated end 15. The modified signal then passes down the detector probe 13 to the Raman equipment 14 for interpretation. FIG. 2 is a view of the treated end 15 of the detector probe 13. It has a roughened surface 16 that is deposited with silver film 17 and then chemisorbed with a molecular-specific coating 18. This molecular-specific coating 18 is uniquely designed to chemically complex with the analyte 19 in the solution surrounding the detector probe end 15 holding the analyte sufficiently near the roughened surface 16 so that it can be detected upon proper exposure to the laser light 9.

EXAMPLE ONE

The class of analytes first studied was metal ions since they do not possess vibrational modes so were undetected by Raman spectroscopy. The molecular-specific coating was the Raman indicator Eriochrome Black T, abbreviated EBT. This EBT (80%, Aldrich) was purified in accordance with K. Carron et al, *Applied Spectroscopy*, 45, 420, (1991), which is herein incorporated by reference, and hereinafter referred to as Carron (1991).

The enhancement coating of the SERS substrate, formed by using 50 nm mass thickness of silver film deposited over $CaF_2$, with EBT was as demonstrated by Carron (1991).

The EBT possessed excellent analyte specific Raman bands since the complexed metal ion shifted the Raman lines in a characteristic, easily detectable, manner. Resonance enhanced SERS, often signified as SERRS, measurements were performed in a standard manner as explained by Carron (1991).

In particular alkaline earth metal ions were employed to ascertain the standard resolving power of EBT. The SERRS resolving power of combinations Ca-Mg, Sr-Mg, and Ba-Mg was 0.40, 3.22, and 3.57 respectively; contrariwise, using absorption spectroscopy, the corresponding results were 0.01, 0.22, and 0.30 respectively. For these results, a resolving power greater than unity indicated a successful resolution can be obtained between the two species as further explained by Carron (1991).

The indicated SERRS results showed that by using EBT as a Raman indicator only Ca-Mg would not be resolved, whereas none of the subject combinations could be resolved by absorption spectroscopy.

EXAMPLE TWO

Similar experimental results as explained above in Example 1 were made using $Pb^{+2}$ where the detection limit was about 270 ppb. This somewhat disappointing value was explained by the use of intensity differences in closely occurring Raman spectral lines of 1274 and 1325 $cm^{-1}$ for this $EBT/Pb^{+2}$ complexing. Carron (1991) elaborated on this difficulty and indicated that with expected improvements, such as longer integration times, the ultimate detection limit for $Pb^{+2}$ would be approximately 50 ppb.

EXAMPLE THREE

Similar experimental results as explained above in Example 2 were made using $Cu^{+2}$ where the detection limit was about 85 ppb. For this case the Raman spectral lines utilized were 1274 and 1403 $cm^{-1}$ for this EBT-/$Cu^{+2}$ complex. Better sensitivity was realized due to copper's lower molecular weight. The details were explained by Carron (1991) indicating that with expected improvements, such as a longer integration time, the ultimate detection limit for $Cu^{+2}$ would be approximately 16 ppb.

EXAMPLE FOUR

A fiber-optic surface was prepared to act as an SERS substrate. The molecular-specific coating or analyte was cobalt phthalocyanine, referred to as CoPc, and obtained commercially from Kodak. Carron (1985) explained the previous use of CoPc for SERS. Testing this CoPc coated on fiber-optic probes which had deposited a silver film of 60, 50, 30, 20, and 15 nm mass thickness proceeded with varying roughness imparted to the substrate by polishing papers containing alumina particles of 0.3, 3, 15, and 32 micrometers in roughness. Significant enhancement in the Raman signal was obtained in all cases. The best mode was 20 nm silver mass thickness covering a surface pre-roughened with 32 micrometer polishing paper and this produced a general enhancement of approximately five orders of magnitude over normal Raman spectroscopy.

EXAMPLE FIVE

For the detection of organic compounds the molecular-specific coating was a partitioning compound which selectively positioned the required organic compounds onto the previously metal coated fiber-optic surface. The series of compounds selected was alkyl thiols making an inert coating.

A SERS substrate was prepared using silver film of mass thickness 5 nm for enhancement that had been pre-roughened by etching with 30% $HNO_3$, rinsed with distilled water and allowed to air dry. The roughened silver substrate was the immersed in a 14 mM solution of octadecyl mercaptan (98%, Aldrich), one of the alkyl thiols, in absolute ethanol (Quantum) for 24 hours at room temperature in order to bond the partitioning compound to the surface. Substrates were stored under distilled water between uses.

Aqueous solutions of mixed xylenes, benzene, p-dichlorobenzene and naphthalene were prepared using distilled water. The substrate was exposed to each solution for periods of 15 minutes to 24 hours, to allow time for partitioning to occur. A SERS spectrum of the organic in the solution in contact with the substrate was then obtained showing good response to the organic molecules.

Additionally vapor phase detections were obtained using silver film surfaces between the analyte and the substrate. These produced the detection limits in molar concentrations of $5.08(10^{-3})$, $3.59(10^{-5})$, and $4.69(10^{-6})$ respectively for benzene, p-dichlorobenzene, and naphthalene.

EXAMPLE SIX

A series of Raman pH-indicators involving amphoteric, sometimes referred to as amphiprotic, compounds was demonstrated. In particular Cresol Red, Methyl Red, and 4-pyridine thiol were employed and were picked by measuring their Raman peak intensity differences over a desirable pH range. Said Raman indicators (Aldrich) were initially modified with dicyclohexylcarbodiimide, commonly referred to as DCC (Aldrich), and cystamine (Aldrich) to form disulfides. The SERS surface was exposed to solution of the disulfide to form the anchored thiolate of said indicators by chemisorption. This surface was exposed to aqueous solutions each of a different pH. Methyl Red was found to accurately correlate with pH between pH values of 2 and 4.5. Cresol Red was found to be an accurate Raman pH indicator over the range of pH from 2 to 8. The 4-pyridine thiol exhibited pH Raman peak intensity changes but appeared less advantageous than either Cresol Red or Methyl Red.

As an example a molecular-specific coating to detect hydrogen ions, or otherwise a pH Raman sensor, was constructed using Cresol Red on an optical fiber to monitor the pH change of water as acetic acid was added. The fiber tip was initially roughened with optical polishing paper. The tip was then coated with 35 nm of silver and immersed in a solution of the disulfide form of Cresol Red to assemble a layer of the Raman indicator. The Raman arrangement shown in FIGS. 1 and 2 was used to monitor pH.

These examples show that molecular-specific coatings of Raman indicators and partitioning compounds can be found that will perform satisfactory in complexing/partitioning with the subject analytes to be measured by SERS. Some of these experiments were performed on laboratory SERS substrates; however, placing these systems on fiber-optic probes can be easily accomplished as noted by Examples Four and Six.

The foregoing description of the specific embodiments will so fully reveal the general nature of the invention that others can, by applying current knowledge, readily modify and/or adapt for various applications such specific embodiments without departing from the generic concept, and therefore such adaptations or modifications are intended to be comprehended within the meaning and range of equivalents of the disclosed embodiments. It is to be understood that the phraseology or terminology herein is for the purpose of description and not of limitation.

We claim:

1. A process for molecular-specific coating of SERS fiber-optic probes comprising:
   providing a fiber-optic SERS probe;
   providing a molecular-specific coating; and
   bonding by chemisorption, absorption, or adsorption said molecular-specific coating onto said probe.

2. The process according to claim 1 wherein said molecular-specific coating further comprises a Raman indicator compound for ions.

3. The process according to claim 2 wherein said ions further comprise the alkaline earth metal ions.

4. The process according to claim 3 wherein said metal ions comprise calcium, magnesium, barium, strontium, copper or lead.

5. The process according to claim 2 wherein said Raman indicator consists essentially of Eriochrome Black T.

6. The process according to claim 1 wherein said molecular-specific coating further comprises amphiprotic compounds as a Raman pH indicator.

7. The process according to claim 6 wherein said amphiprotic compounds comprise Cresol Red, Methyl Red, or 4-pyridine thiol.

8. The process according to claim 6 wherein said Raman pH indicator consists essentially of Cresol Red.

9. The process according to claim 1 wherein said molecular-specific coating further comprises a partitioning compound for organic molecules.

10. The process according to claim 9 wherein said partitioning compound for organic molecules further comprises alkyl thiols.

11. The process according to claim 10 wherein said alkyl thiols consists essentially of octadecyl mercaptan.

12. The process according to claim 9 wherein said organic molecules comprise xylenes, benzene, p-dichlorobenzene, or naphthalene.

13. The process according to claim 1 wherein said bonding by chemisorption, absorption, or adsorption said molecular-specific coating onto said probe further comprises requiring the difference in SERS bands associated with the coating and the coating/analyte complex be proportional to quantitative amounts of the analyte.

14. A process for Raman indicator coating of SERS fiber-optic probes comprising:
   providing a SERRS probe roughened to about 32 micrometers and film deposited to about 15 to 60 nm mass thickness with silver; and
   chemisorping a molecular-specific coating on said probe.

15. The process according to claim 14 wherein said molecular-specific coating further comprises Eriochrome Black T as a Raman indicator for metal ions.

16. The process according to claim 15 wherein said metal ions comprise calcium, magnesium, barium, strontium, copper or lead.

17. The process according to claim 14 wherein said molecular-specific coating further comprises octadecyl mercaptan as a Raman partitioning compound for organic molecules.

18. The process according to claim 17 wherein said organic molecules comprise xylenes, benzene, p-dichlorobenzene, or naphthalene.

19. The process according to claim 14 wherein said molecular-specific coating further comprises amphiprotic compounds as a Raman pH indicator.

20. The process according to claim 19 wherein said amphiprotic compounds comprise Gresol Red, Methyl Red, or 4-pyridine thiol.

21. The product produced according to the process of claim 1.

22. The product produced according to the process of claim 14.

23. A process for molecular-specific coating of SERS fiber-optic probes comprising:
   providing a fiber-optic SERS probe with a roughened surface subsequently covered with thin metal film;
   providing a molecular-specific coating; and bonding by chemisorption, absorption, or adsorption said molecular-specific coating onto said probe.

24. The process according to claim 23 wherein said roughened surface comprises using polishing paper containing alumina particles of about from 0.3 to 32 micrometers in roughness.

25. The process according to claim 23 wherein said thin metal film further comprises gold, silver, or copper.

26. The process according to claim 23 wherein said thin metal film further comprises a mass thickness of about 15 to 60 nm.

* * * * *